(12) United States Patent
Hazard et al.

(10) Patent No.: US 7,775,982 B2
(45) Date of Patent: Aug. 17, 2010

(54) METHOD AND SYSTEM FOR SUB-APERTURE PROCESSING

(75) Inventors: Christopher Robert Hazard, Niskayuna, NY (US); Bruno Hans Haider, Ballston Lake, NY (US); Douglas Glenn Wildes, Ballston Lake, NY (US); Reinhold Bruestle, Zipf (AT); Armin Schoisswohl, Wels (AT); Kjell Kristoffersen, Oslo (NO)

(73) Assignee: General Electric Company, Niskayuna, NY (US)

(*) Notice: Subject to any disclaimer, the term of this patent is extended or adjusted under 35 U.S.C. 154(b) by 914 days.

(21) Appl. No.: 11/611,423

(22) Filed: Dec. 15, 2006

(65) Prior Publication Data
US 2008/0146938 A1   Jun. 19, 2008

(51) Int. Cl.
*G01N 9/24* (2006.01)
(52) U.S. Cl. .............................. 600/462; 73/602
(58) Field of Classification Search .............. 600/462; 73/602
See application file for complete search history.

(56) References Cited

U.S. PATENT DOCUMENTS

| | | | |
|---|---|---|---|
| 5,832,923 A | 11/1998 | Engeler et al. | |
| 5,997,479 A | 12/1999 | Savord et al. | |
| 6,013,032 A | 1/2000 | Savord | |
| 6,102,860 A | 8/2000 | Mooney | |
| 6,126,602 A | 10/2000 | Savord et al. | |
| 6,491,634 B1 | 12/2002 | Leavitt et al. | |
| 2004/0267126 A1 | 12/2004 | Takeuchi | |
| 2004/0267135 A1 | 12/2004 | Takeuchi | |

FOREIGN PATENT DOCUMENTS

WO    WO02093548 A2    11/2002

*Primary Examiner*—Long V Le
*Assistant Examiner*—Saurel J Selkin
(74) *Attorney, Agent, or Firm*—Jason K. Klindtworth

(57) ABSTRACT

A transducer assembly is provided including a transducer array comprising a plurality 'M' of transducer elements and a sub-aperture processor comprising a plurality 'P' of input channels and an output channel. The plurality 'P' of input channels is coupled to the 'M' transducer elements and a plurality 'R' of switching elements in operative association with the output channel of the sub-aperture processor to switchably couple the output channel to at least one of a plurality of 'N' system channels.

25 Claims, 16 Drawing Sheets

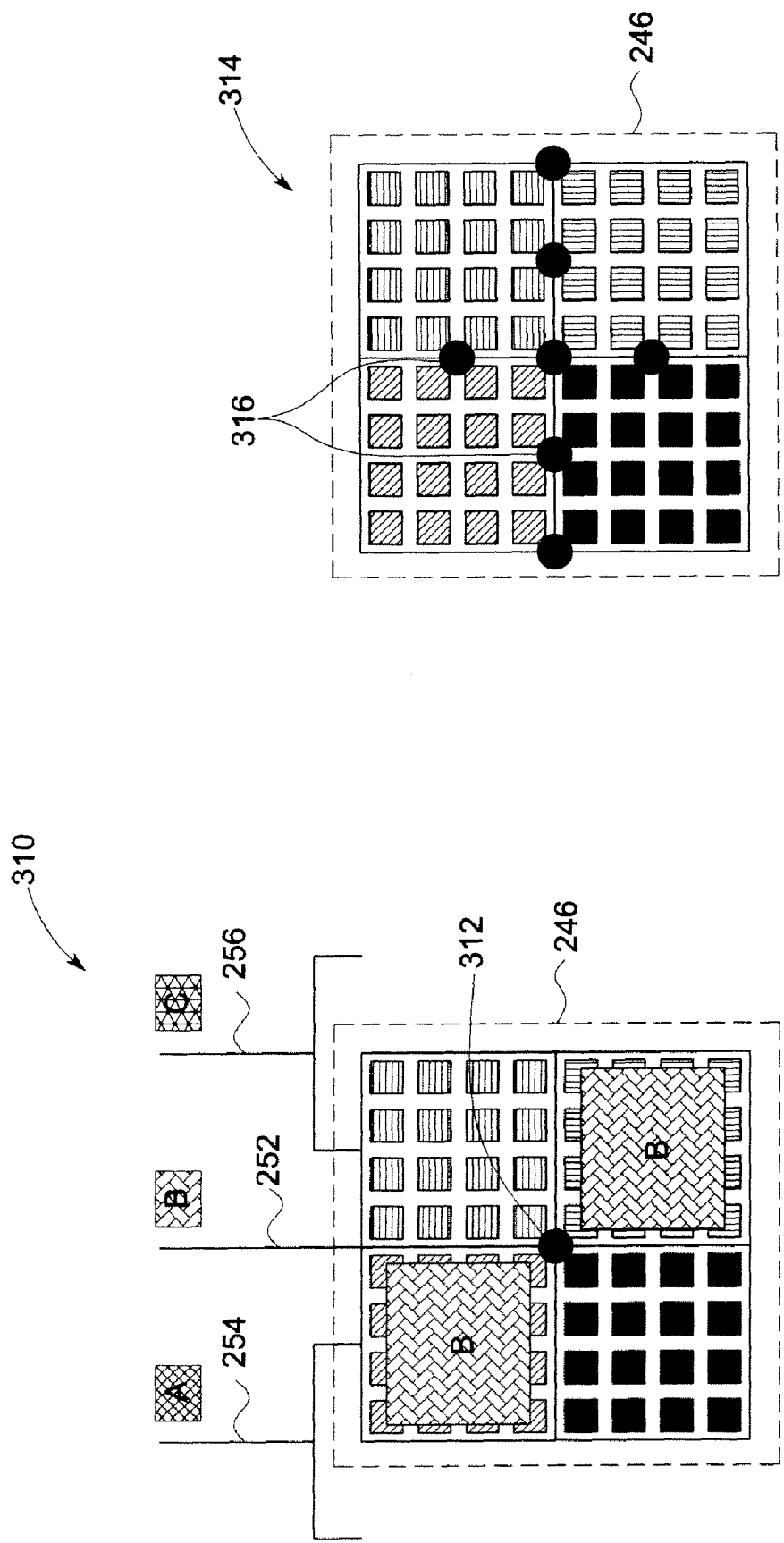

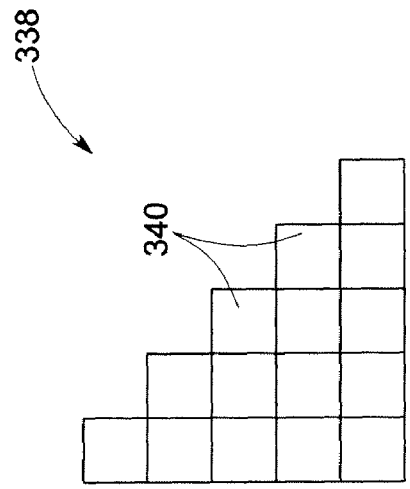
FIG. 17
FIG. 18
FIG. 19

METHOD AND SYSTEM FOR SUB-APERTURE PROCESSING

BACKGROUND

Embodiments of the application relate generally to ultrasound imaging, and more specifically to an arrangement of a plurality of sub-arrays on a transducer array.

Conventional ultrasound imaging systems generally employ an array of transducer elements to transmit an ultrasound beam and subsequently receive a reflected beam from an object under interrogation. As will be appreciated, the array of transducer elements may include an arrangement in which the transducer elements are arranged in a two-dimensional array. Moreover, some ultrasound imaging systems may utilize large two-dimensional arrays of transducer elements often containing between 1000 and 20,000 transducer elements. Unfortunately, such a large number of transducer elements substantially exceeds the number of beamforming channels typically available even in most advanced ultrasound imaging systems.

Previously conceived methods for performing beamforming on such large arrays of transducer elements utilize configurable transducer arrays in which transducer elements having similar delays are grouped together. However, while the delays for the connected transducer elements may be similar, the delays may not be identical, thereby resulting in delay errors. In certain situations these delay errors may be within acceptable limits. However, as the number of transducer elements connected to a beamforming channel increases, the delay errors may become unacceptable. An alternative solution for applications that employ a large number of transducer elements is the use of sub-aperture processors (SAPs) to reduce the number of system channels required to process signals from the large number of transducer elements. However, use of the conventional SAPs may not provide the complete, dynamic delay required to beamform the signal.

Furthermore, currently available beamforming techniques propose altering the shape of the sub-apertures coupled to the sub-aperture processor as a function of the beam direction. As will be appreciated, altering of the shape of the sub-apertures involves changing the transducer elements that are connected as inputs to the sub-aperture processors. For example, the reconfigurable nature of the transducer element inputs imposes stricter requirements on the amplifiers which receive signals from the elements. Most notably, noise associated with switching inputs to the SAP may be amplified by the amplifier in the SAP, thereby necessitating use of very low noise switching. Also, the large impedance of the small transducer elements makes switching difficult. Furthermore, since the transducer elements are also used to transmit acoustic energy, the switches typically require high voltage, thus making the switch circuits large and less suitable for the application.

BRIEF DESCRIPTION

Briefly, in accordance with aspects of the present technique, a transducer assembly is presented. The transducer assembly includes a transducer array having a plurality 'M' of transducer elements and a plurality 'N' of system channels. Further, the transducer assembly includes a sub-aperture processor comprising a plurality 'P' of input channels and an output channel, where the plurality 'P' of input channels is coupled to the 'M' transducer elements. In addition, the transducer assembly includes a plurality 'R' of switching elements in operative association with the output channel of the sub-aperture processor to switchably couple the output channel to at least one of the 'N' system channels.

In accordance with further aspects of the present technique a transducer assembly is presented. The transducer assembly includes a plurality 'K' of sub-aperture processors, wherein each of the 'K' sub-aperture processors comprises a plurality of input channels and an output channel, wherein the transducer assembly is adapted such that each output channel is switchably connectable to a plurality 'N' of system channels.

In accordance with yet another aspect of the present technique an ultrasound system is presented. The ultrasound system includes an acquisition subsystem configured to acquire ultrasound data, where the acquisition subsystem includes a transducer array comprising a plurality 'M' of transducer elements, a plurality 'N' of system channels, a sub-aperture processor comprising a plurality 'P' of input channels and an output channel, wherein the plurality of 'P' of input channels is coupled to the 'M' transducer elements, and a plurality 'R' of switching elements in operative association with the output channel of the sub-aperture processor to switchably couple the output channel to at least one of the 'N' system channels. Furthermore, the ultrasound system includes a processing subsystem configured to process the ultrasound data acquired via the acquisition subsystem.

In accordance with further aspects of the present technique, a method of imaging is presented. The method includes receiving by a first plurality of transducer elements, one or more signals representative of imaging data. Also, the method includes processing the one or more signals by a first sub-aperture processor coupled to the first plurality of transducer elements. In addition, the method includes switchably coupling an output signal from the first sub-aperture processor to a selected plurality of system channels.

In accordance with another aspect of the present technique, a transducer assembly is further presented. The transducer assembly includes a transducer array comprising a plurality 'M' of transducer elements and a sub-aperture processor comprising a plurality 'P' of input channels and an output channel, wherein the plurality 'P' of input channels is coupled to the 'M' transducer elements. The transducer assembly further includes switching logic having a switch input and a plurality of switch outputs, wherein the switch input is coupled to the output channel and each of the plurality of switch outputs is selectively connectable to the switch input.

DRAWINGS

These and other features, aspects, and advantages of the invention will become better understood when the following detailed description is read with reference to the accompanying drawings in which like characters represent like parts throughout the drawings, wherein:

FIG. 1 a block diagram of an exemplary transducer assembly, in accordance with aspects of the present technique;

FIG. 13 depicts a location of a virtual element in a sub-aperture processor, in accordance with aspects of the present technique;

FIG. 14 illustrates an example configuration having several possible virtual element locations for different sub-aperture processor configurations;

FIG. 17 illustrates another example configuration of a sub-aperture package, in accordance with aspects of the present technique;

FIG. 18 illustrates yet another example configuration of a sub-aperture package, in accordance with aspects of the present technique;

FIG. 19 illustrates another example configuration of a sub-aperture package, in accordance with aspects of the present technique;

DETAILED DESCRIPTION

Figure 1:
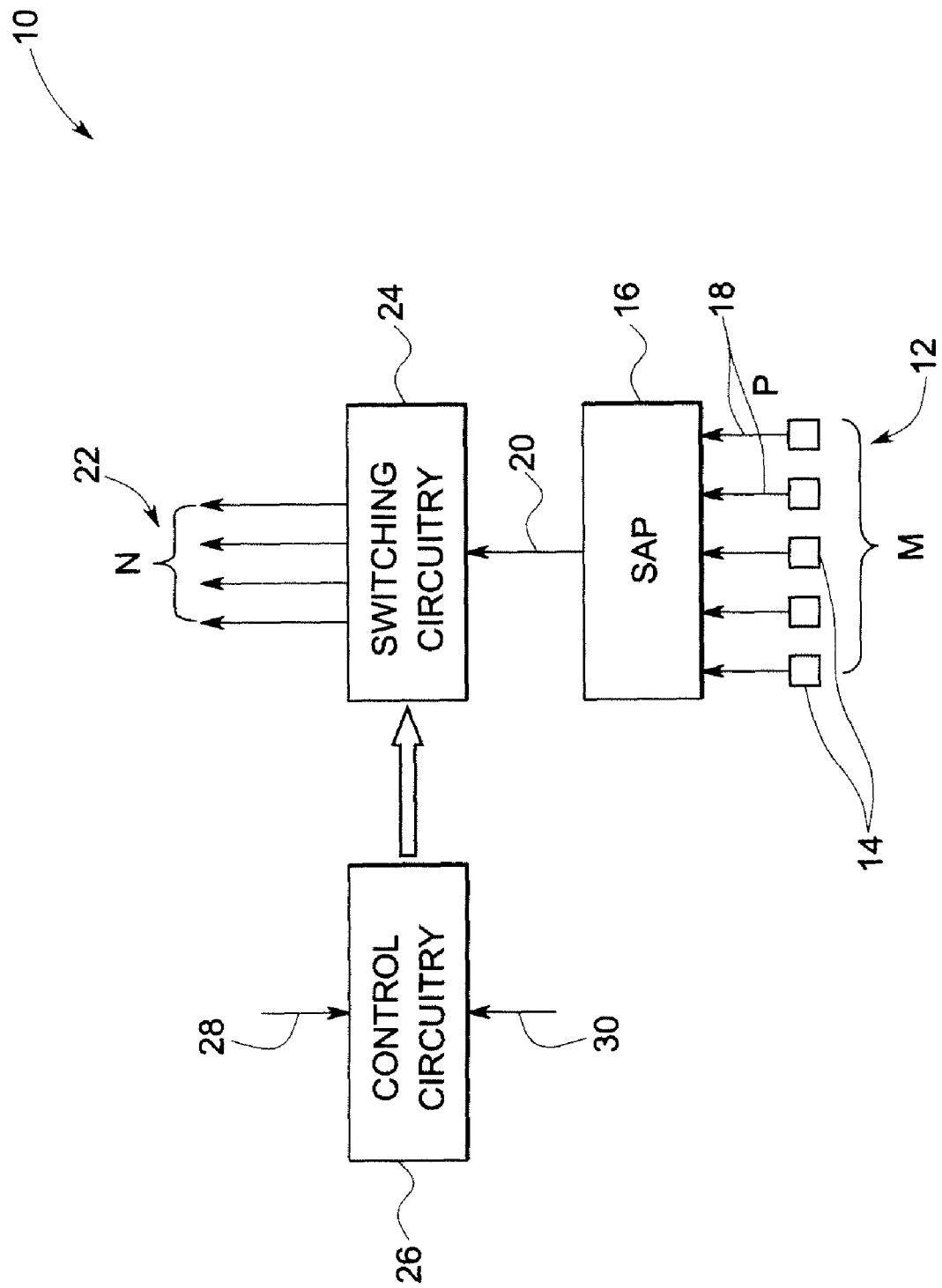

FIG. 1 illustrates an exemplary embodiment of a transducer assembly 10. In accordance with aspects of the present technique, the transducer assembly 10 may include a transducer array 12, where the transducer array 12 may include two or more (e.g., represented as 'M') transducer elements 14. In certain embodiments, the transducer elements 14 may include capacitive micromachined transducer elements, lead zirconate titanate (PZT) transducer elements, polyvinylidene difluoride (PVDF) transducer elements, or other transducer elements either known in the art or to be identified, as well as combinations thereof.

Further, the transducer assembly 10 may include one or more sub-aperture processors (SAPs) 16. In the illustrated embodiment of FIG. 1, a single SAP 16 is shown. However, certain transducer assemblies may include two or more (e.g., represented as 'K') SAPs. As will be appreciated, sub-aperture processors (SAPs) may be employed in transducer arrays having a relatively large number of transducer elements to allow a reduced number of system beamformer channels to process signals from the relatively large number of transducer elements. Further, the SAP typically processes signals from a group of transducer elements by applying local beamforming delays among those signals. This delayed group of signals may then be summed and the resulting summed signal sent to a conventional beamformer for further delay, apodization, summing and processing.

The SAP 16 may include two or more (e.g., represented as 'P') input channels 18 and at least one output channel 20. The input channels 18 may be configured to facilitate coupling of the transducer elements 14 to the SAP 16. It may be noted that in certain embodiments, the number of input channels 18 may be equal to the number of transducer elements 14. Alternatively, the number of input channels 18 may be different from the number of transducer elements 14.

Additionally, the transducer assembly 10 may include two or more (e.g., represented as 'N') system beamformer channels 22. The terms 'system beamformer channels' and 'system channels' may be used interchangeably herein. The transducer assembly 10 may also include switching circuitry 24. In one embodiment, the switching circuitry 24 may include switching logic such as a plurality of switching elements (not shown) including, but not limited to micro-electromechanical system (MEMS) switches or solid state switches. Further, the switching elements may be in operative association with the output channel 20 of the SAP 16 and may be configured to switchably couple the output channel 20 to at least one of the system beamformer channels 22.

The transducer assembly 10 may also include a controller 26 configured to control selection of the system channel(s) 22 to be operatively coupled with the output channel 20 of the SAP 16. In one embodiment, the controller 26 is coupled to the switching circuitry 24 to control switching between the output channel 20 and the one or more system channel(s) 22. The controller 26 may facilitate switching of switching circuitry 24 based upon various input parameters including e.g., a local sub-aperture geometry 30, a beam geometry 28 or a combination thereof, and will be described in greater detail with reference to FIGS. 5-13.

The controller 26 may be implemented in hardware (e.g., using various electronic components), in software, or the controller 26 may include a combination of both hardware and software. For example, the controller 26 may be implemented as an application specific integrated circuit (ASIC), a programmable logic device, a microcontroller, or a special purpose processor. The controller 26 may further include volatile or non-volatile memory to store data, instructions, or control codes to effect control of switching circuitry 24. In other embodiments, the controller 26 may include an electrically erasable programmable read only memory (EEPROM), wherein software routines are executed in place from the EEPROM.

According to aspects of the present technique, the transducer assembly 10 illustrated in FIG. 1 may be designed for use in probes configured to facilitate interventional procedures. In the illustrated embodiment of FIG. 1, the transducer assembly 10 may accordingly be of a size or dimension suitable for use in an invasive probe employed in space-constrained applications, for example. In certain embodiments, the invasive probe may include an imaging catheter, an endoscope, a laparoscope, a surgical probe, a transesophageal probe, a transvaginal probe, a transrectal probe, an intracavity probe, or a probe adapted for interventional procedures. Additionally, the transducer assembly 10 may be designed for use in applications, such as, but not limited to intracardiac echocardiography, pediatric echocardiography, transesophageal echocardiography, pediatric echocardiography, and laparoscopic surgery.

Figure 2:
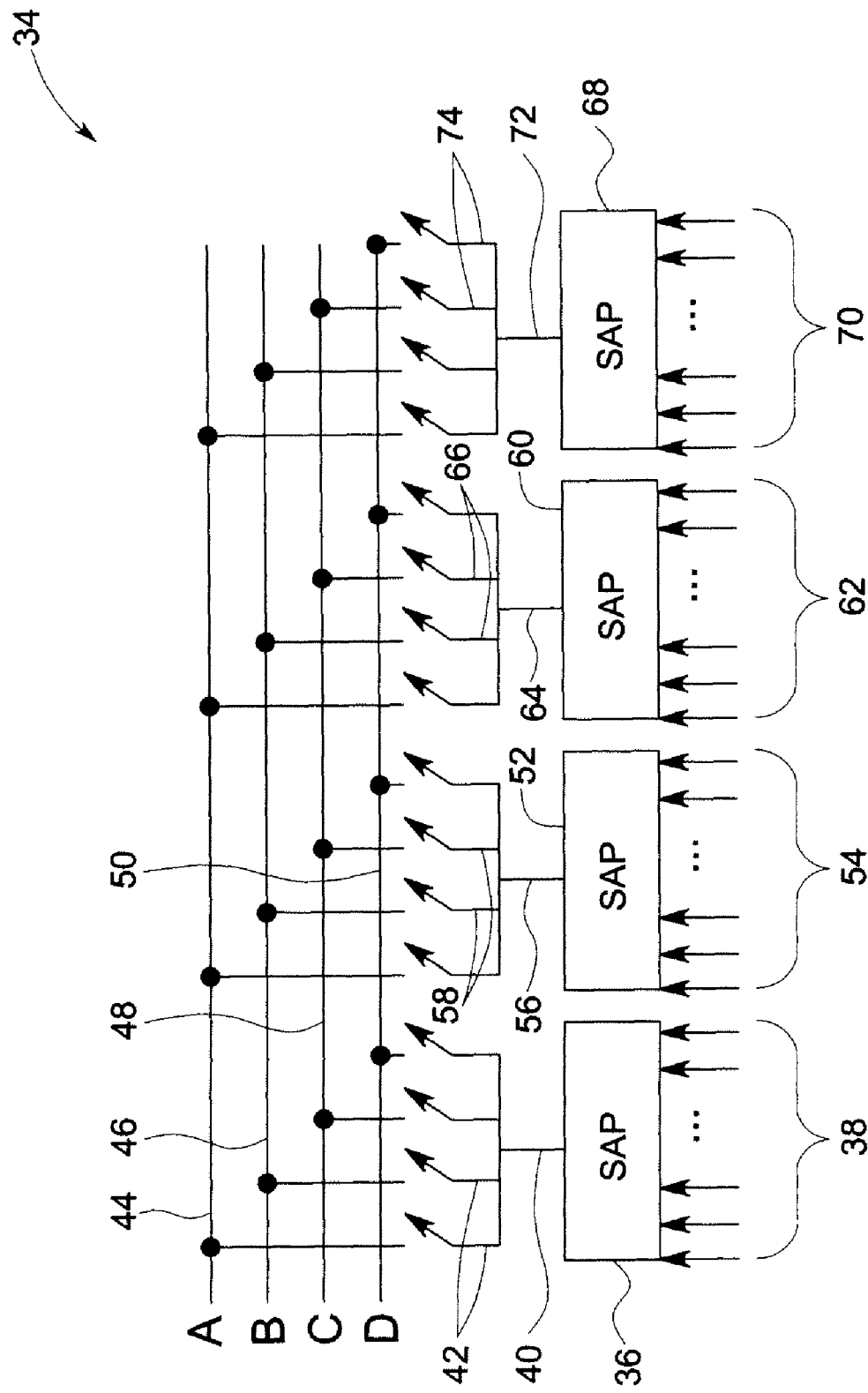
FIG. 2 is an exemplary embodiment of a transducer assembly, in accordance with aspects of the present technique.

As described hereinabove, FIG. 1 illustrates one embodiment of the transducer assembly 10 including one SAP 16, wherein the output channel 20 of the SAP 16 is in operative association with at least one system channel 22. Turning now to FIG. 2, one embodiment of a transducer assembly 34 having a plurality of sub-aperture processors (SAPs), where respective output channels of the SAPs are coupled to one or more system channels is illustrated. In the illustrated embodiment of FIG. 2, the transducer assembly 34 is shown as including four SAPs, however transducer assemblies having fewer or greater number of SAPs are also envisaged in accordance with aspects of the present technique.

As depicted in FIG. 2, the illustrated transducer assembly 34 may include a first SAP 36, a second SAP 52, a third SAP 60 and a fourth SAP 68. The first SAP 36 may include a first set of input channels 38 configured to be operatively coupled to transducer elements (not shown), as noted with reference to FIG. 1. In addition, the first SAP 36 may include a first one or more output channels 40. Furthermore, the transducer assembly 34 may be configured to couple to one or more system beamformer channels. In the illustrated embodiment of FIG. 2, the transducer assembly 34 is shown as including connections to a first system beamformer channel 'A' 44, a second system beamformer channel 'B' 46, a third system beamformer channel 'C' 48 and a fourth system beamformer channel 'D' 50. Additionally, the transducer assembly 34 may include a first set of switching elements 42 configured to switchably couple the first one or more output channels 40 to at least one of the system beamformer channels 44, 46, 48, 50.

The second SAP 52 may include a second set of input channels 54 and a second one or more output channels 56. Additionally, the second one or more output channels 56 may be operationally coupled to at least one of the system channels 44, 46, 48, 50 via a second set of switching elements 58, as previously noted. The third SAP 60 may include a third set of input channels 62 and a third one or more output channels 64. A third set of switching elements 66 may be employed to couple the third one or more output channels 64 to at least one of the system channels 44, 46, 48, 50. Furthermore, the fourth SAP 68 may include a fourth set of input channels 70 and a fourth one or more output channels 72. The fourth one or more output channels 72 may be operatively coupled to at least one of the system channels 44, 46, 48, 50 via a fourth set of switching elements 74. In transducer assembly configurations that utilize an additional number of SAPs beyond those illustrated in FIG. 2, additional switching elements may be used.

Figure 3:
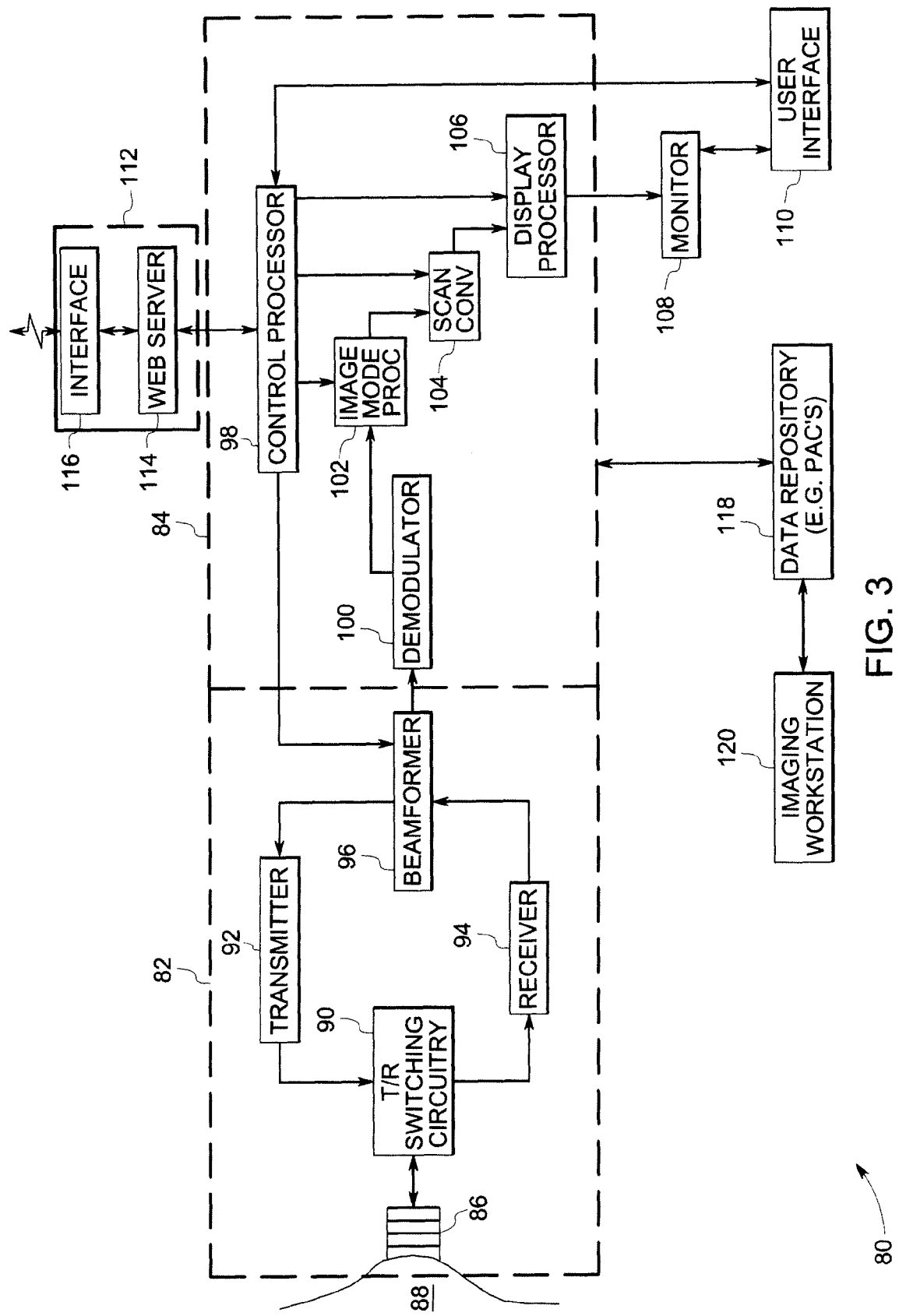
FIG. 3 is one embodiment of an ultrasound imaging system.

FIG. 3 is a block diagram of an example ultrasound system 80 including a transducer array 86 configured in accordance with one embodiment of the present invention. As illustrated, the ultrasound system 80 may include an acquisition subsystem 82 and a processing subsystem 84. The acquisition subsystem 82 may include the transducer array 86 (having a plurality of transducer array elements), transmit/receive switching circuitry 90, a transmitter 92, a receiver 94, and a beamformer 96. The processing subsystem 84 may include a control processor 98, a demodulator 100, an imaging mode processor 102, a scan converter 104 and a display processor 106. The display processor 106 may be further coupled to a display monitor 108 for displaying images, while the user interface 110 may interact with the control processor 98 and the display monitor 108. The control processor 98 may also be coupled to a remote connectivity subsystem 112 to provide remote access to at least a portion of ultrasound system 80. The remote connectivity subsystem 112 may include e.g., a web server 114 and a remote connectivity interface 116. The processing subsystem 84 may be further coupled to a data repository 118 configured to receive and store ultrasound image data. The data repository 118 interacts with an imaging workstation 120.

The aforementioned components may include dedicated hardware elements such as circuit boards with digital signal processors or may represent functional software components designed for execution on a general or special-purpose computer or processor. The various components may be combined or separated according to various embodiments of the invention. Thus, it should be appreciated that the present ultrasound system 80 is provided by way of example, and the present techniques are in no way limited by the specific system configuration.

In the acquisition subsystem 82, the transducer array 86 is intended to be placed in contact with a patient or subject 88. The transducer array 86 may be coupled to the transmit/receive (T/R) switching circuitry 90. The T/R switching circuitry 90 may in turn be coupled to the output of transmitter 92 and the input of the receiver 94. The output of the receiver 94 is configured as an input to the beamformer 96. As illustrated, the beamformer 96 further may be coupled to the input of the transmitter 92 and to the input of the demodulator 100. The beamformer 96 also may be coupled to the control processor 98 as shown in FIG. 3.

In the processing subsystem 84, the output of demodulator 100 is coupled to an input of an imaging mode processor 102. The control processor 98 interfaces with the imaging mode processor 102, the scan converter 104 and the display processor 106. An output of imaging mode processor 102 is coupled to an input of scan converter 104. An output of the scan converter 104 is coupled to an input of the display processor 106. The output of display processor 106 is coupled to the monitor 108.

The ultrasound system 80 transmits ultrasound energy into the subject 88 and receives and processes backscattered ultrasound signals from the subject 88 to create and display an image. To generate and transmit a beam of ultrasound energy, the control processor 98 sends command data to the beamformer 96 to generate transmit parameters to create a beam of a desired shape originating from a certain point at the surface of the transducer array 86 at a desired steering angle. The transmit parameters are sent from the beamformer 96 to the transmitter 92. The transmitter 92 uses the transmit parameters to properly encode transmit signals to be sent to the transducer array 86 through the T/R switching circuitry 90. The transmit signals are set at certain levels and phases with respect to each other and are provided to individual transducer elements of the transducer array 86. The transmit signals excite the transducer elements to emit ultrasound waves with the same phase and level relationships. As a result, a transmitted beam of ultrasound energy is formed in a subject 88 within a scan plane along a scan line when the transducer array 86 is acoustically coupled to the subject 88 by using, for example, ultrasound gel. The process is known as electronic scanning.

The transducer array 86 is a two-way transducer. When ultrasound waves are transmitted into a subject 88, the ultrasound waves are backscattered off the tissue and blood samples within the subject 88. The transducer array 86 receives the backscattered waves at different times, depending on the distance into the tissue they return from and the angle with respect to the surface of the transducer array 86 at which they return. The transducer elements convert the ultrasound energy from the backscattered waves into electrical signals.

The electrical signals are then routed through the T/R switching circuitry 90 to the receiver 94. The receiver 94 amplifies and digitizes the received signals and provides other functions such as gain compensation. In one embodiment, the SAP and switching circuitry of FIGS. 1 and 2 may be included within the receiver 94. The digitized received signals corresponding to the backscattered waves received by each transducer element at various times preserve the amplitude and phase information of the backscattered waves.

The digitized signals are sent to the beamformer 96. The control processor 98 sends command data to beamformer 96. The beamformer 96 uses the command data to form a receive beam originating from a point on the surface of the transducer array 86 at a steering angle typically corresponding to the point and steering angle of the previous ultrasound beam transmitted along a scan line. The beamformer 96 operates on the appropriate received signals by performing time delaying and focusing, according to the instructions of the command data from the control processor 98, to create received beam signals corresponding to sample volumes along a scan line in the scan plane within the subject 88. The phase, amplitude, and timing information of the received signals from the various transducer elements is used to create the received beam signals.

The received beam signals are sent to the processing subsystem 84. The demodulator 100 demodulates the received beam signals to create pairs of I and Q demodulated data values corresponding to sample volumes within the scan plane. Demodulation is accomplished by comparing the phase and amplitude of the received beam signals to a reference frequency. The I and Q demodulated data values preserve the phase and amplitude information of the received signals.

The demodulated data is transferred to the imaging mode processor 102. The imaging mode processor 102 generates imaging parameter values from the demodulated data in scan sequence format. The imaging parameters may include parameters corresponding to various possible imaging modes such as B-mode, color velocity mode, spectral Doppler mode, and tissue velocity imaging mode, for example. The imaging parameter values are passed to the scan converter 104. The scan converter 104 processes the parameter data by performing a translation from scan sequence format to display format. The translation includes performing interpolation operations on the parameter data to create display pixel data in the display format.

The scan converted pixel data is sent to the display processor 106 to perform any final spatial or temporal filtering of the scan converted pixel data, to apply grayscale or color to the scan converted pixel data, and to convert the digital pixel data to analog data for display on the monitor 108. The user interface 110 is coupled to the control processor 98 to allow a user to interface with the ultrasound system 80 based on the data displayed on the monitor 108.

Figure 4:
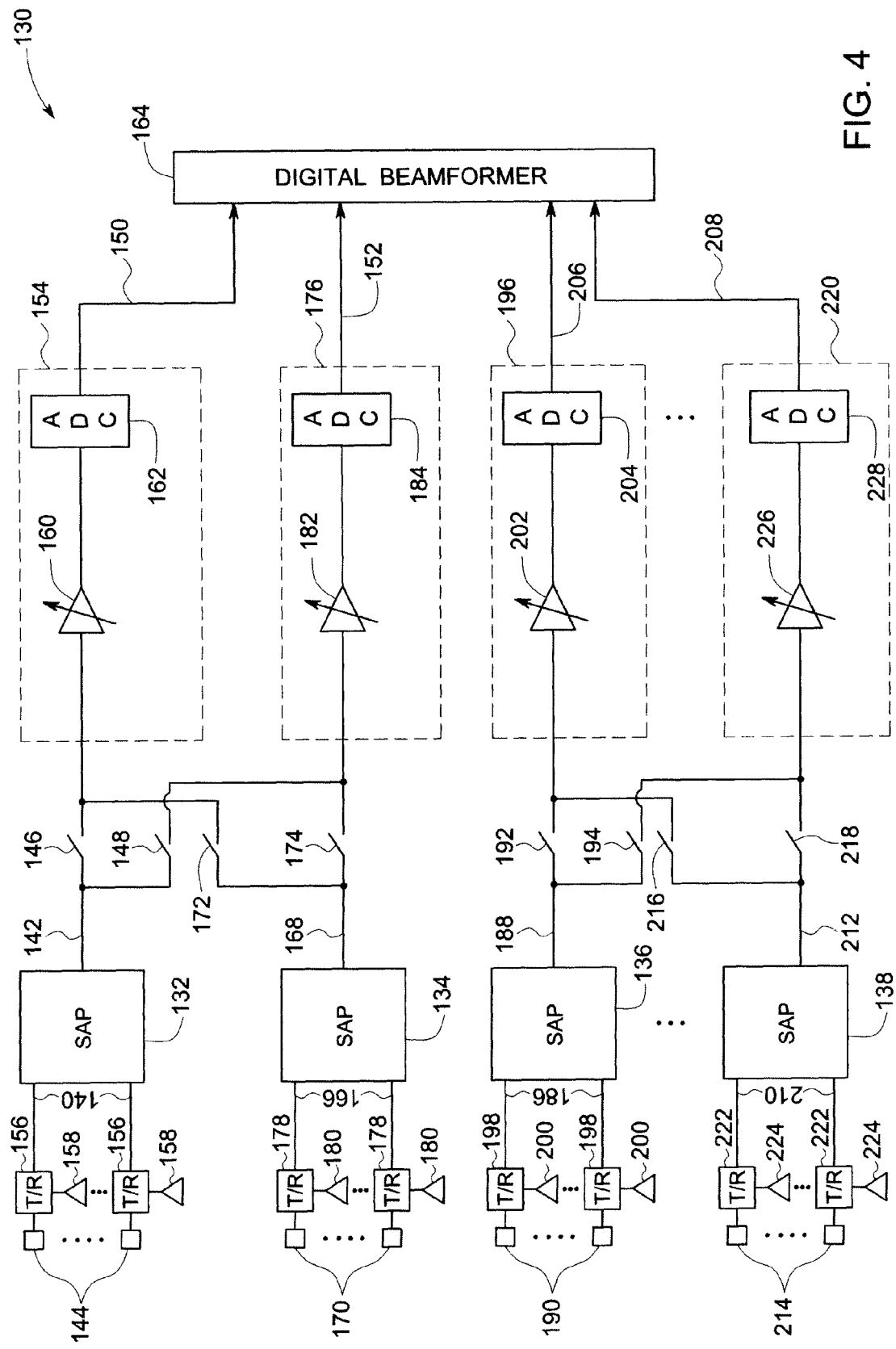
FIG. 4 is an exemplary embodiment illustrating an implementation of sub-aperture processors and switching logic, in accordance with aspects of the present technique.

Turning now to FIG. 4, a block diagram 130 of one embodiment of the acquisition module 82 of FIG. 3 is illustrated. In the illustrated embodiment, an acquisition sub-system 130 is shown as including a transducer array having a plurality of transducer elements, transmit/receive circuitry, sub-aperture processors (SAPs) having input channels and at least one output channel, system channels and switching elements configured to operatively couple the output channels of the sub-aperture processors to at least one system channel.

In the illustrated embodiment, the acquisition sub-system 130 is shown as including 'K' SAPs, where K represents an integer variable greater than 1. For the purposes of the illustrated embodiment of FIG. 4, it will be assumed that K=4. Accordingly, the acquisition sub-system 130 may include a first SAP 132, a second SAP 134, a third SAP 136 and a fourth SAP 138.

Each of the illustrated SAPs (134, 136, 138) may respectively include a set of input channels (140, 166, 186, 210) and at least one output channel (142, 168, 188, 212). Also, a set of transducer elements (144, 170, 190, 214) may be operatively coupled to the SAPs (132, 134, 136, 138) via the respective set of input channels (140, 166, 186, 210). In one embodiment, transmit/receive circuitry (156, 178, 198, 222) and pulsers (158, 180, 200, 224) may be coupled between each of the transducers and the SAPs to help generate a transmit pulse and protect the receivers from high voltages pulses during transmission. Additionally, each output channel (142, 168, 188, 212) may be switchably coupled to at least one system beamformer channel (150, 152, 206, 208) via use of one or more switching elements (146, 148, 172, 174, 192, 194, 216, 218).

In one embodiment, a first switching element 146 and a second switching element 148 may be coupled to the first output channel 142, where the first switching element 146 and the second switching element 148 may be configured to facilitate switchably coupling the output channel 142 of the first SAP 132 to at least one beamformer channel. For example, the first SAP 132 may be switchably coupled to either a first beamformer channel 150 or a second beamformer channel 152. More particularly, the first SAP 132 may be coupled to the first beamformer channel 150 via the first switching element 146, while the second switching element 148 may be configured to facilitate coupling the first SAP 142 to the second beamformer channel 152. Similarly, the second SAP 134 may be coupled to the first beamformer channel 150 via a third switching element 172, or the second SAP 134 may be coupled to the second beamformer channel 152 via a fourth switching element 174. Operation of the switching elements associated with the third and fourth SAPs 136, 138 is substantially similar to that of the first two SAPs and will therefore not be repeated. It should be noted that although each SAP is depicted as being selectively coupled to two system beamformer channels, such is intended to be illustrative and not limiting. For example, one or more SAPs could be selectively coupled to more than two system beamformer channels and each SAP need not be selectively coupled to the same number of system beamformer channels.

In one embodiment, one or more preprocessors may be communicatively coupled between a SAP and a respective beamforming channel. In the illustrated embodiment of FIG. 4, four preprocessors (154, 176, 196, 220) are shown. Each preprocessor may include a variable gain amplifier (160, 182, 202, 226) and an analog-to-digital converter (ADC) (162, 184, 204, 228) coupled together. Signals received from a SAP may then be processed via the variable gain amplifier 160 and the ADC. In other words, a digital signal representative of the analog input to the ADC may be generated subsequent to processing via the ADC. The digital signal that is output from the ADC may then be provided to a digital beamformer 164.

Figure 5:
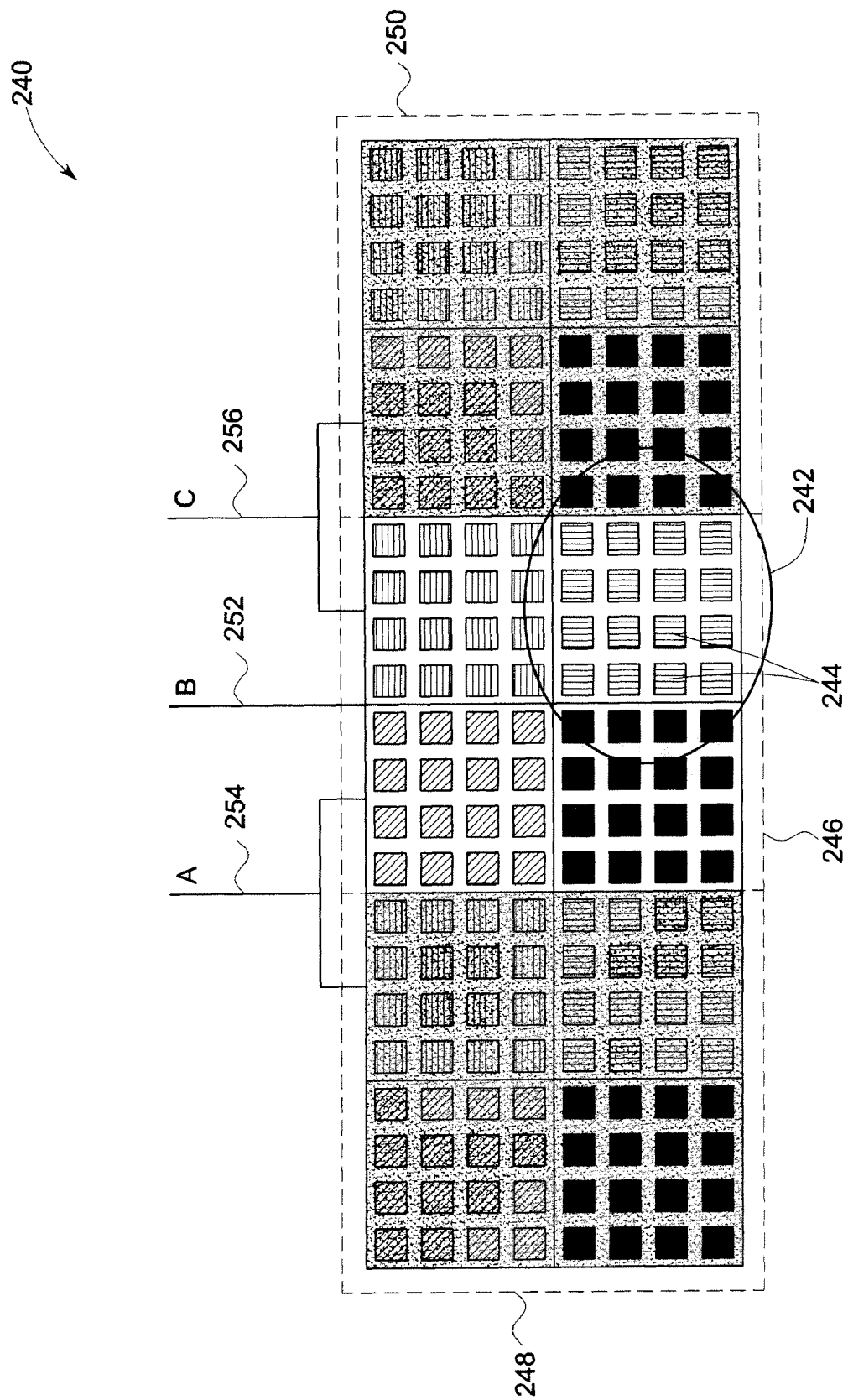
FIG. 5 illustrates a physical grouping of transducer elements and a logical grouping of sub-aperture processors, in accordance with aspects of the present technique.

Referring now to FIG. 5, one embodiment of a physical grouping of transducer elements and a logical grouping of SAPs is illustrated. Reference numeral 242 is representative of a SAP. In the illustrated embodiment, the SAP 242 is defined by a group of transducer elements that is arranged in a 4×4 pattern resulting in a total of 16 inputs to the SAP.

In accordance with further aspects of the present technique, a group of four SAPs, such as the SAP 242, may be arranged to form a package 246 of four SAPs. This package of four SAPs 246 may generally be referred to as a QuadSAP package 246. In a presently contemplated configuration, the four SAPs may be arranged such that the QuadSAP package 246 has a square shape, as illustrated in FIG. 5. More particularly, the four individual SAPs may be arranged in a 2×2 pattern, where each of the four SAPs includes a 4×4 arrangement of transducer elements 244. Further, a second QuadSAP package 248 and a third QuadSAP package 250 that are formed similar to the QuadSAP package 246 may be disposed adjacent to the QuadSAP package 246, as depicted in the embodiment of FIG. 5.

In addition, the QuadSAP packages 246, 248, 250 may include one or more system channels 252, 254, 256. As previously noted, the output channels of the SAPs may be switchably coupled to at least one system channel. More particularly, the output channels of the SAPs may be switchably coupled to more than one system channel. In other words, in certain embodiments, the system channels may be "shared" between the outputs of the SAPs or an "exclusive" system channel may be configured to service a single one SAP or SAP package in a dedicated manner.

With continuing reference to FIG. 5, the illustrated grouping of SAPs 240 may be configured to include a first system channel 'B' 252, a second system channel 'A' 254 and a third system channel 'C' 256. More particularly, in a presently contemplated configuration, system channel 'B' 252 may be configured to be "exclusively" coupled to the outputs of the SAPs in the QuadSAP package 246, and may be referred to as exclusive channel 'B' 252. Further, system channel 'A' 254 may be "shared" between the outputs of SAPs in QuadSAP packages 246 and 248 and may be referred to as a first shared system channel 'A' 254. Similarly, system channel 'C' 256 may be "shared" between the outputs of the SAPs in QuadSAP packages 246 and 250 and may be referred to as a second shared system channel 'C' 256. Accordingly, in one embodiment, the individual outputs of each of the four SAPs 246 in the QuadSAP structure 242 may be operatively coupled to at least one of the system channels 'A' 254, 'B' 252 or 'C' 256. Similarly, the outputs of the SAPs in the QuadSAP packages 248, 250 may be operatively coupled to the shared system channels 'A' 254 and 'C' 256, in accordance with aspects of the present technique.

This structure may also be extended to any number of QuadSAP structures and is not necessarily limited to the three QuadSAP packages illustrated in FIG. 5. Additionally, the grouping of SAPs 240 may be repeated over multiple rows to form a larger 2D array. In the example illustrated in FIG. 5, each QuadSAP may be configured to be operatively coupled with at least two system channels. Consequently, about 4×16=64 elements may be handled by two system beamformer channels. As will be appreciated, this accounts for a 1/32 reduction in the number of system channels that would otherwise be required to handle data from the transducer elements in the 2D array. Moreover, the number of system channels required in a QuadSAP design can be decreased by a factor of 2 over a single SAP design. More specifically, in a single SAP design, one system channel is required for each SAP. Thus, in a single SAP design, 4 system channels would be required for 64 elements as compared to 2 system channels for the same number of elements in a QuadSAP design.

It may also be noted that the number and arrangement of SAPs in the packages, such as the grouping 250 may vary. The number of dedicated or exclusive system channels (for example, system channel 'B' 252 in the illustrated example) may also be varied. In a similar fashion, the number of shared system channels (for example, system channels 'A' 254 and 'C' 256 in the illustrated example) may be varied. Furthermore, in accordance with aspects of the present technique, the system channels 252, 254, 256 may be shared vertically, horizontally (as depicted in FIG. 5), and/or diagonally. The size and shape of the sub-apertures associated with the individual SAPs, such as SAP 242, may also be varied. This technique may also be combined with the concept of shape-changing sub-apertures. All of these abovementioned parameters allow a tradeoff between flexibility and complexity, where the tradeoffs for different applications may be different.

Figure 6:
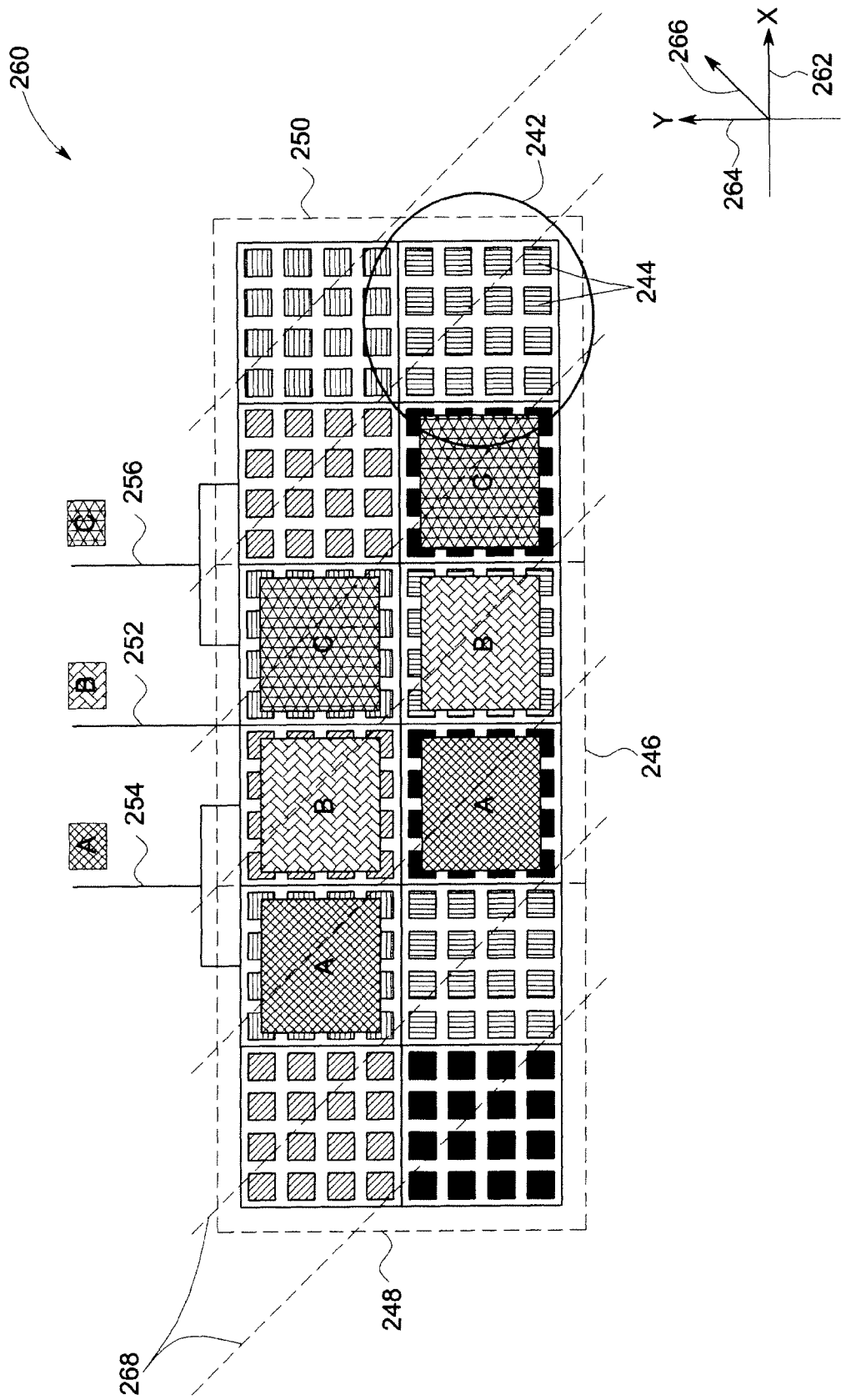
FIG. 6 is an exemplary example of configuring switching elements coupled to the output channels of sub-aperture processors for a particular beam, in accordance with aspects of the present technique.

Turning now to FIG. 6, an example switching configuration 260 illustrating switching elements coupled to the output channels of SAPs for a particular beam is shown. As previously noted, the outputs of the SAPs, such as SAP 242, within the QuadSAP packages 246, 248, or 250 may be switchably coupled to the system channels 252, 254, 256. More particularly, in accordance with aspects of the present technique, the outputs of the SAPs may be switchably coupled to the system channels 252, 254, 256 such that errors caused by the limited delay capability of the SAPs is minimized.

Accordingly, a method is presented for switchably coupling the outputs of the SAPs to the system channels 252, 254, 256 such that the errors caused by the limited delay capability of the SAPs is minimized. FIG. 6 illustrates one example of how the switching elements coupled to the output channels of the SAPs may be configured for a particular beam. Reference numeral 262 is representative of an X-axis, while a Y-axis is represented by reference numeral 264. Also, a beam direction may be generally represented by reference numeral 266, while logical lines 268 are representative of lines drawn on the grouping of SAPs 240 (see FIG. 5) in a direction substantially perpendicular to the beam direction 266.

Further, as previously noted the delays associated with the SAPs is known to vary most quickly in a direction substantially perpendicular to the logical lines 268. In accordance with aspects of the present technique, outputs of SAPs that fall on lines 268 may be selected to be grouped together. In other words, outputs of those SAPs may be grouped together for which the delays are most similar. For example, the outputs of the SAPs indicated as 'A' may be operatively coupled the shared system channel 'A' 254, while the outputs of the SAPs indicated as 'C' may be operatively coupled the shared system channel 'C' 256. Similarly, the outputs of the SAPs indicated as 'B' may be operatively coupled to the exclusive channel 'B' 252 via switching elements.

With continuing reference to FIG. 6, a method of imaging may include receiving a first set of one or more signals via a first set of transducer elements. Subsequently, the first set of signals may be processed by a first SAP that is in operative association with the first set of transducer elements to generate a first processed signal. The first processed signal from the first SAP may then be switchably coupled to a one or more system channels.

In a similar fashion, a second set of signals may be received via a second set of transducer elements. Also, a second SAP that is operatively coupled to the second set of signals may be employed to process the second set of signals to generate a second processed signal. Further, the first processed signal and the second processed signal generated by the first and second SAPs may be switchably coupled to at least one shared system channel. Moreover, as previously described with reference to FIG. 1, the signals output from the transducer elements in each of the first and second SAPs may be switchably coupled to a system channel based at least in part upon a determined beam geometry, a transducer element geometry or a combination thereof. For example, the output signals from the first and second SAPs may be switchably coupled to the system channels based upon an orientation of transducer elements in the first and second SAPs to the beam direction. More particularly, processed signals output by the first and second SAPs that are disposed in a direction substantially orthogonal to the beam direction may be coupled to a shared system channel, so as to decrease potential errors.

The method of imaging described hereinabove may be better understood with reference to FIG. 6. Various sets of signals may be received by each of the SAPs 242 in the respective QuadSAP packages 246, 248, 250 from the respective sets of transducer elements that are in operative association with the SAPs. The respective sets of signals may then be processed by each of the SAPs in the QuadSAP packages 246, 248, 250. The output signals generated by each of the SAPs may then be switchably coupled to at least one system channel via switching elements, as previously described.

Furthermore, as previously noted, the output signals from the SAPs are switchably coupled to a system channel, such as system channels 252, 254, 256, such that the errors generated by the limited delay capability of the SAPs is minimized. Accordingly, in one embodiment, output signals from SAPs that are disposed in a direction that is substantially orthogonal to the beam direction 266 are coupled to the same system channel. For example, SAPs indicated by 'A' may be operationally coupled to the shared system channel A 254. Also, SAPs indicated by 'B' that are part of QuadSAP package 246 may be operatively associated with the exclusive channel 'B' 252. Similarly, SAPs indicated by 'C' may be operationally coupled to the shared system channel C 256.

By implementing the method of imaging as described hereinabove, a reduction in the number of required system channels may be achieved for a given number of transducer elements. Such a reduction in system channels may contribute to reduced cost of the system beamformer and a reduced number of required cables among other advantages.

Figure 7:
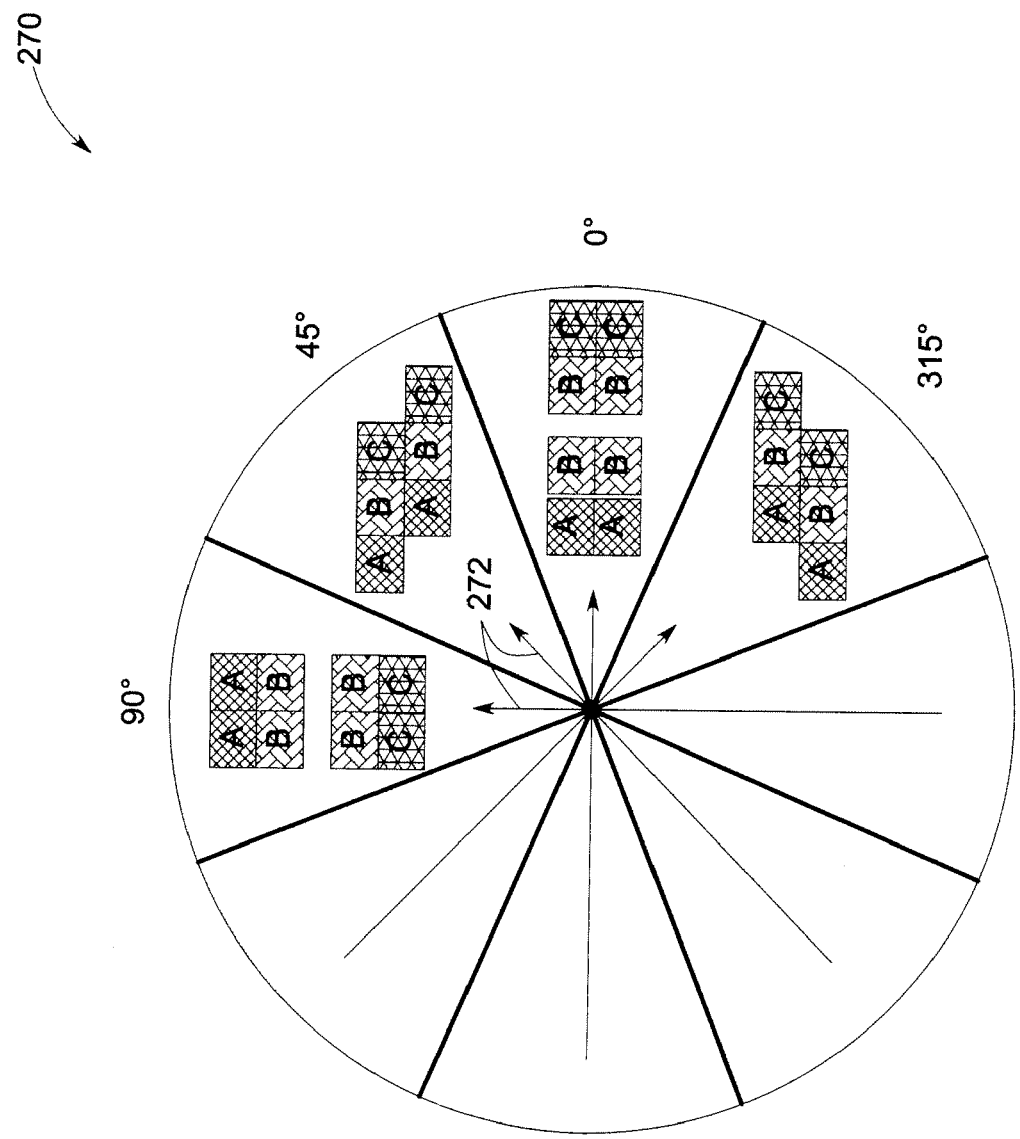
FIG. 7 illustrate various possible configurations of grouping the outputs of sub-aperture processors as a function of the angle of the plane containing the beam, in accordance with aspects of the present technique.
Figure 20:
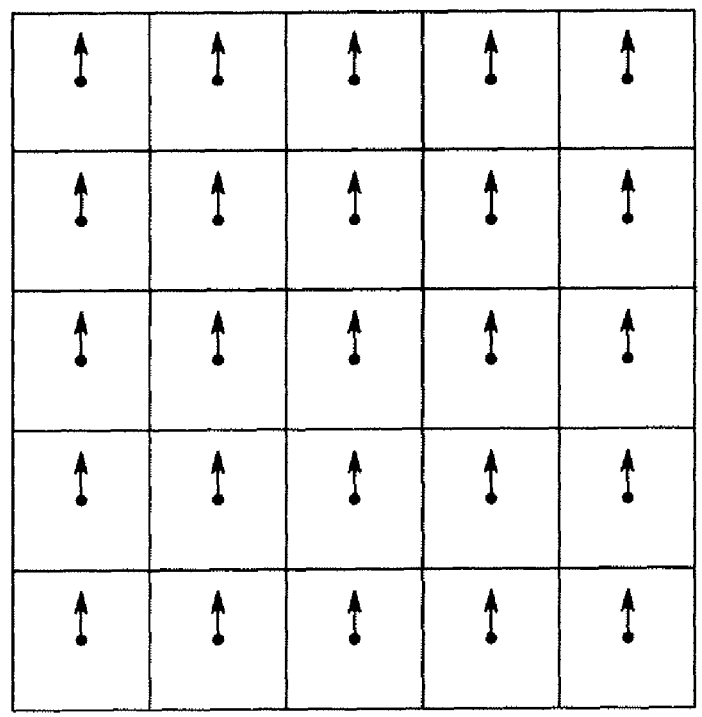
FIG. 20 illustrates one embodiment of a SAP grouping in which a group of SAPs is configured in accordance with a global beam direction.

In accordance with further aspects of the present technique, several configurations for grouping the outputs of the SAPs are presented. FIG. 7 depicts various possible configurations for grouping the outputs of the SAPs as a function of the angle of the plane containing the beam. It may be noted that in FIG. 7, beam directions are generally represented by reference numeral 272. Furthermore, in accordance with aspects of the present technique, a configuration may be chosen globally for all QuadSAPs based e.g., on the direction of the desired beam. The direction of the beam can be characterized by a vector that extends from the phase center of the array (usually the geometric center of the array) to the focal point of interest. This vector can be characterized by a set of angles, such as the angle between the z-axis and the vector and the angle of the projection of the vector into the X-Y plane. Here it is assumed that the coordinate system is such that the transducer array is in the X-Y plane and the z-axis is perpendicular to the transducer and travels through the phase center (i.e. the phase center is the origin). The angle of the projected vector is typically the most important for configuring the QuadSAP. Using the global beam direction means that this angle will be constant for all the QuadSAPs and thus the control may be simplified. This is further illustrated in FIG. 20.

Figure 21:
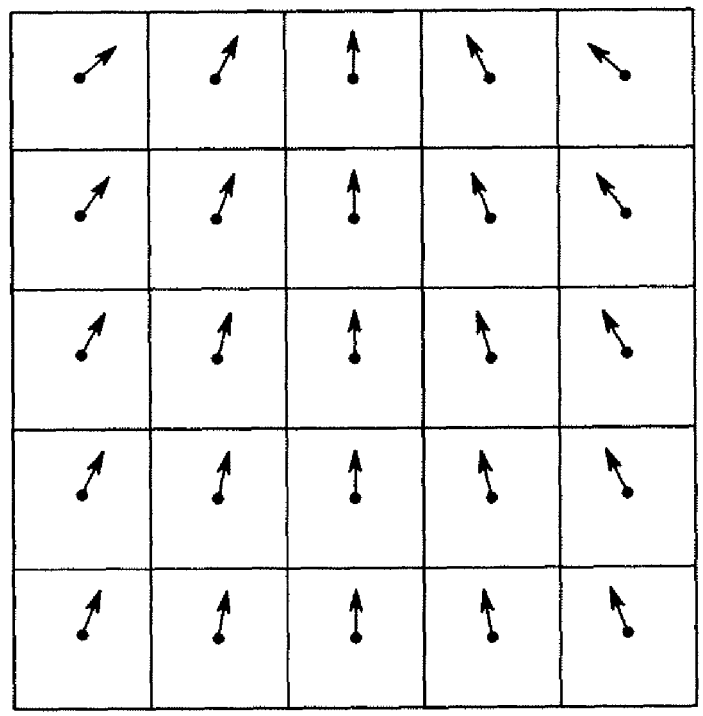
FIG. 21 illustrates another embodiment of a SAP grouping in which a group of SAPs is configured in accordance with a local steering direction.

Alternatively, the configuration for each of the QuadSAPs may be chosen based on the local beam direction. The local beam direction is determined by a vector from the local phase center of the QuadSAP to the focal point. Once again, a projection of that vector on to the plane which contains the QuadSAP is typically the important parameter. In this case that vector is different for every QuadSAP and thus the control is more complex. This is further illustrated in FIG. 21. It may be noted that control of the QuadSAP configuration may be relatively complex in the case where the QuadSAP configuration is selected based on the local beam direction.

Figure 8:
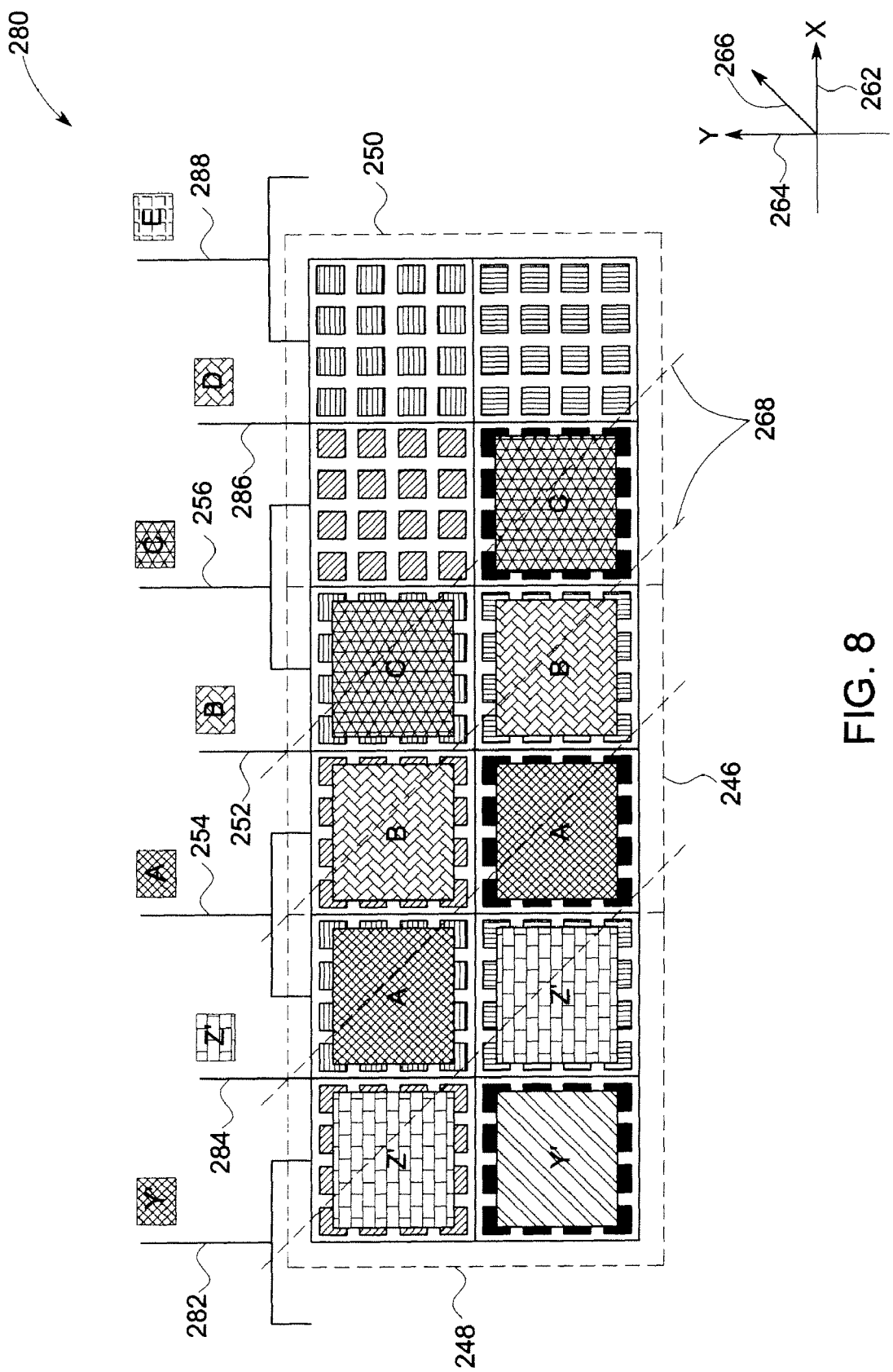
FIGS. 8-12 illustrate examples of sub-aperture processor configurations having inconsistent boundaries, in accordance with aspects of the present technique.
Figure 9:
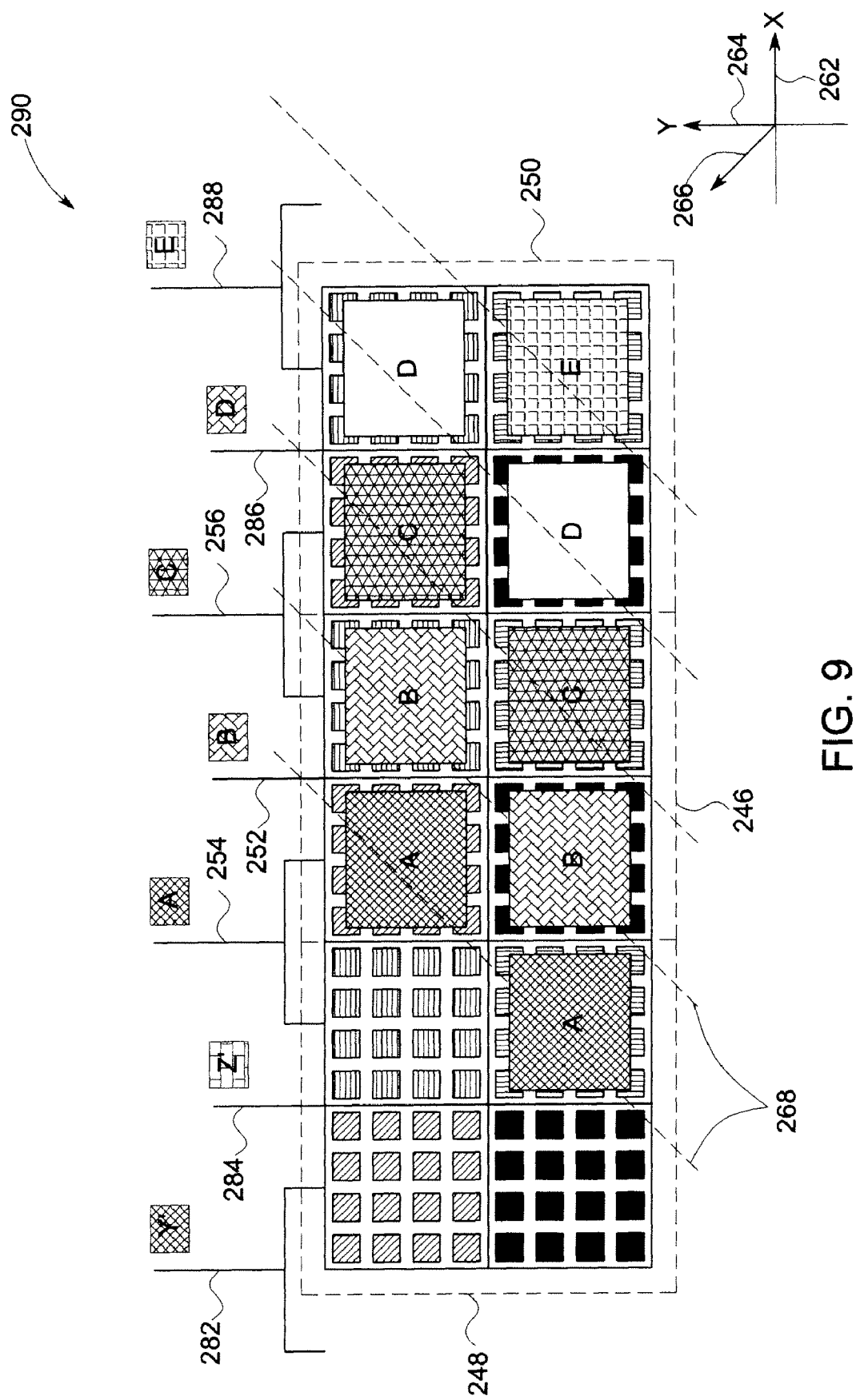

Whether the configuration for each of the QuadSAPs is chosen based on a global beam direction or a local beam direction, the configurations of neighboring QuadSAPs may be incompatible at some boundaries. Referring now to FIGS. 8-12, examples of SAP configurations having such inconsistent boundaries are illustrated. FIGS. 8-9 depict a QuadSAP configuration, such as QuadSAP 246, where two neighboring QuadSAPs, such as QuadSAPs 248 and 250 have different configurations. More particularly, the QuadSAP 246 may be configured to have different configurations (as illustrated between FIG. 8 and FIG. 9) to match with the configuration of QuadSAP 248 and QuadSAP 250. Reference numerals 282 and 288 are representative of shared channel 'Y' and shared channel 'E' respectively. Exclusive channel 'Z' that is configured to be exclusive to QuadSAP 248 may be represented by reference numeral 284. Also, a channel 'D' that is exclusive to QuadSAP 250 may be represented by reference numeral 286. In other words, the configuration of the QuadSAP 246 may be different depending on a local configuration and configurations of the neighboring QuadSAPs such as QuadSAPs 248, 250 in the illustrated example.

Figure 10:
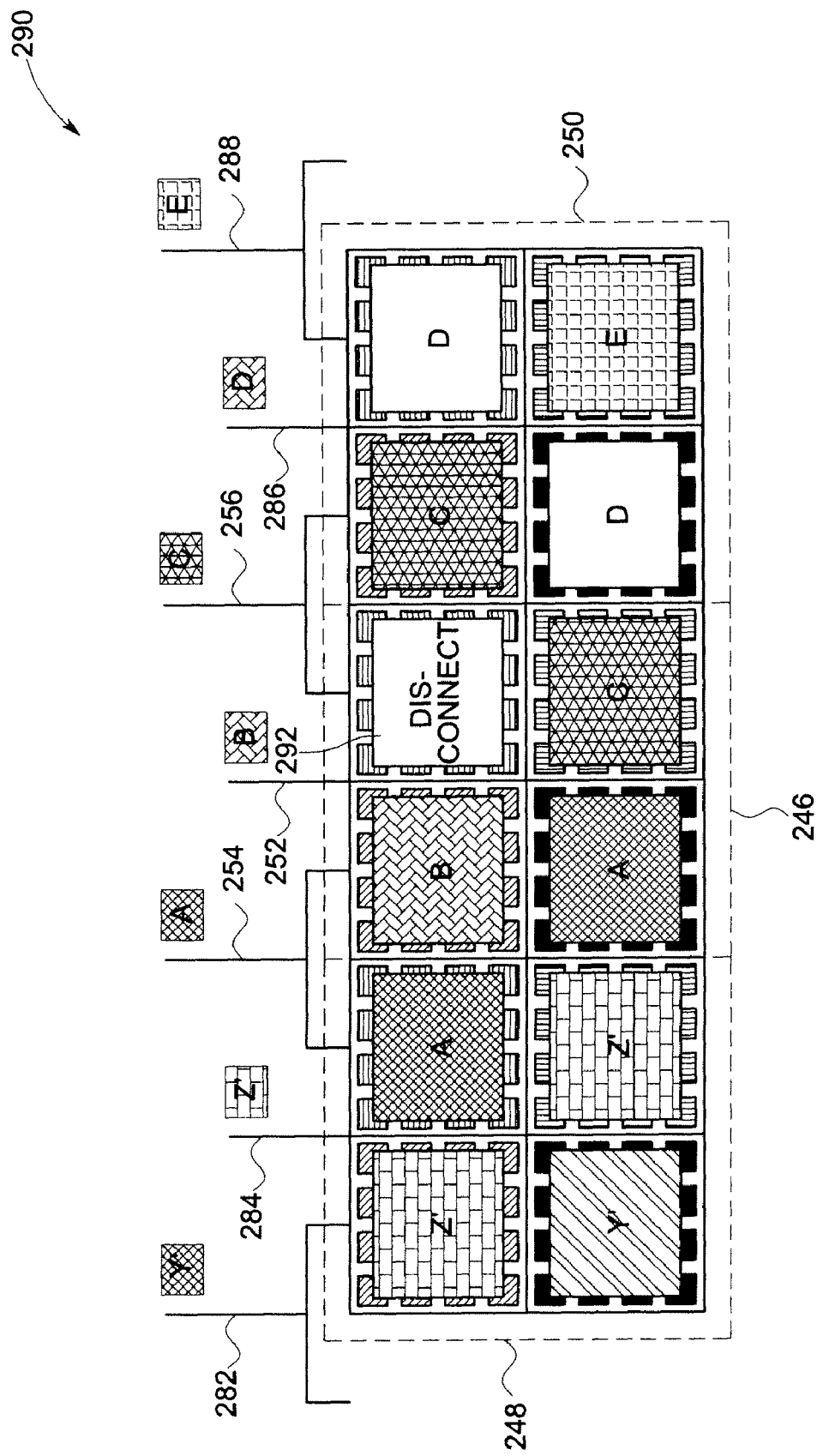
Figure 11:
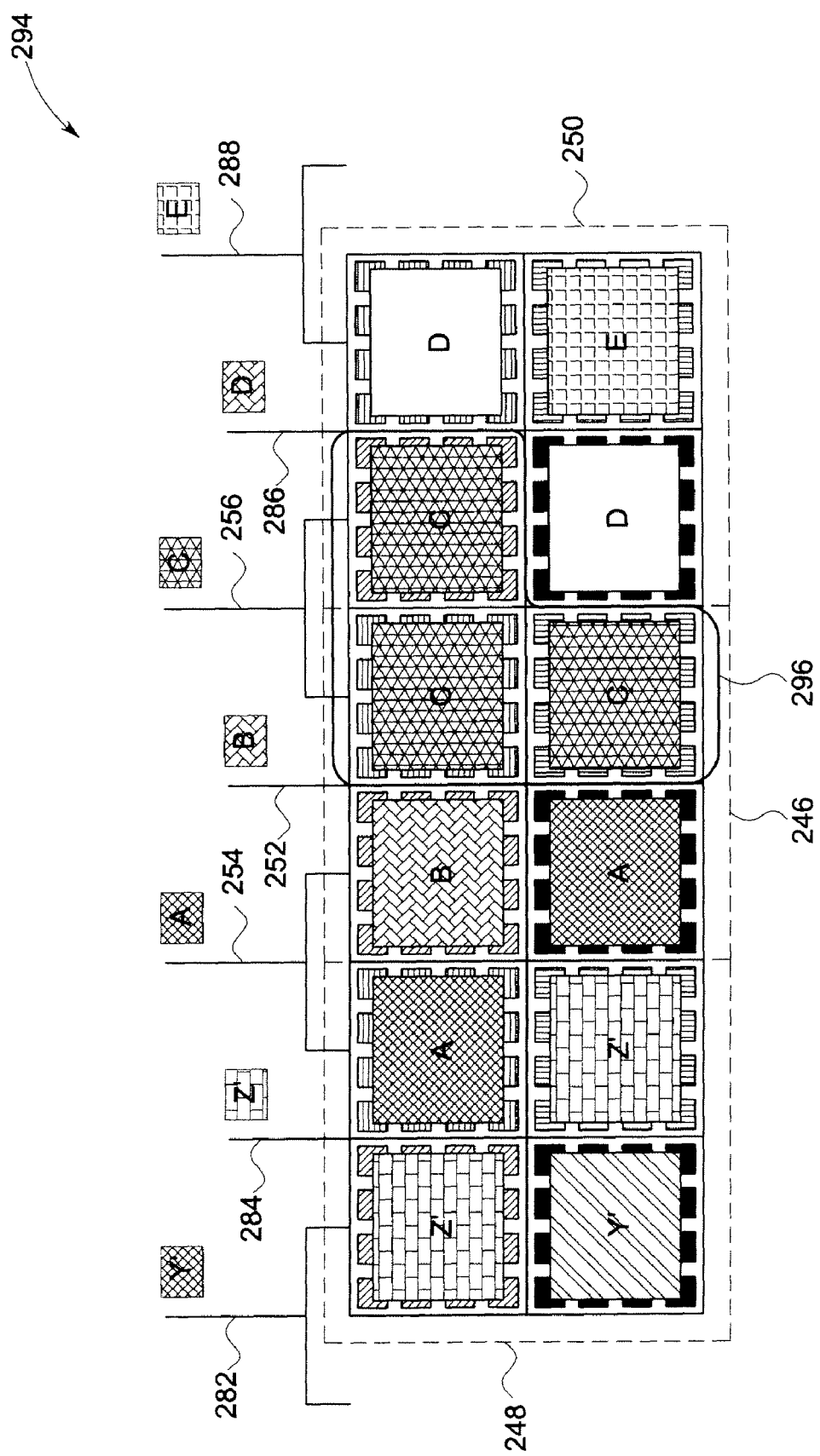
Figure 12:
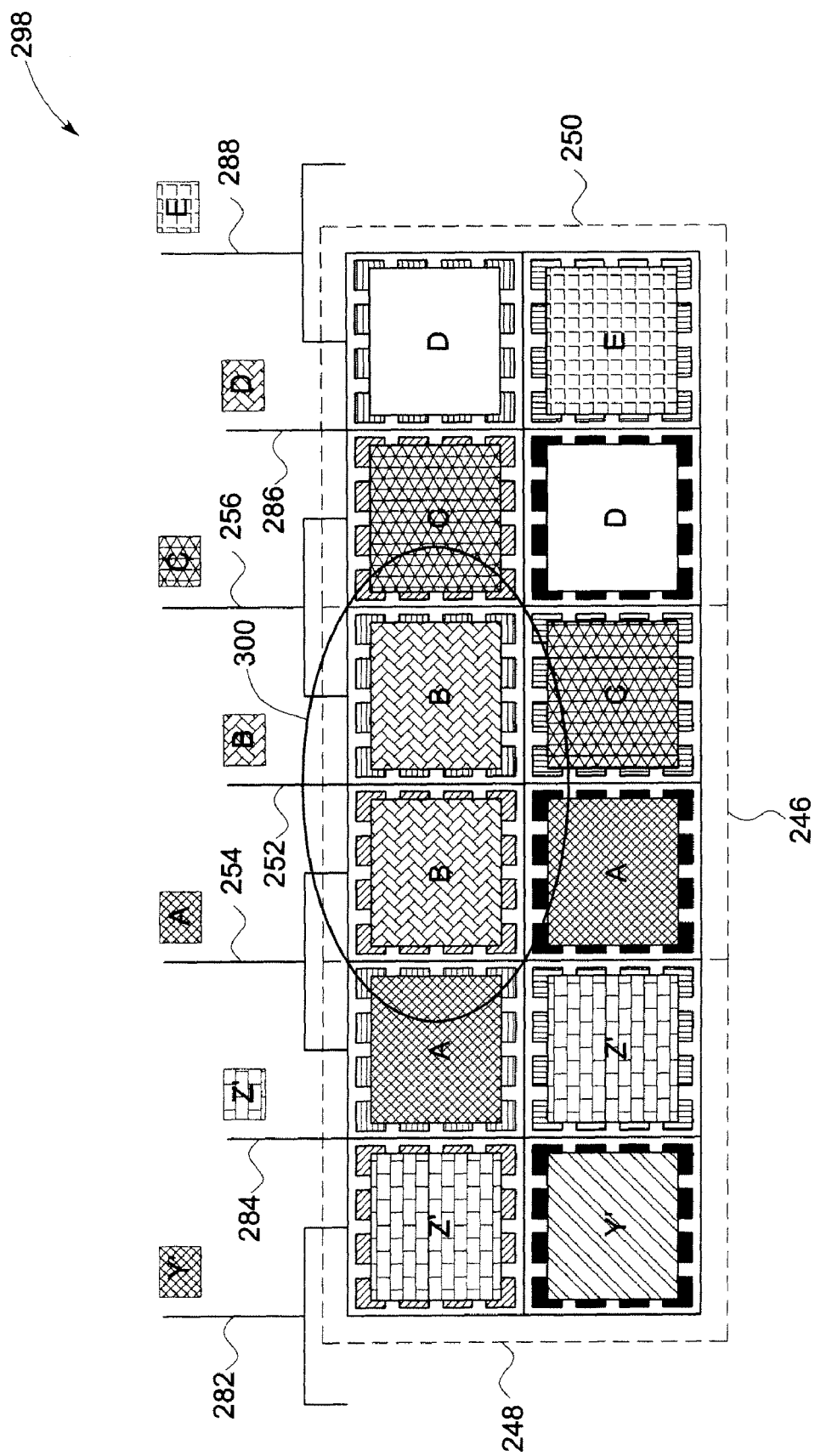

FIGS. 10-12 illustrate three possible solution configurations for cases in which neighboring desired configurations are not compatible. As illustrated in the examples depicted in FIGS. 10-12, a SAP may be connected in a non-optimal way with a system channel, where the system channel may be connected to other SAPs. Alternatively a SAP may be left unconnected, such as SAP 292. It may be noted that a particular imaging situation may be employed to determine an optimal solution of connecting SAPs to a given system channel.

Referring now to FIG. 11, another configuration 294 of SAPs is depicted. In the configuration 294 illustrated in FIG. 11, a group 296 of three SAPs indicated by 'C' may be operatively coupled to the same shared channel 'C' 256. Further, in FIG. 12, an example 298 of a configuration 300 in which horizontally neighboring SAPs are connected to a shared system channel B 252 at the same time diagonally neighboring SAPs are connected to shared system channels (e.g., 284, 254, 256, 286).

Additionally, the system beamformer channels may be configured to delay the outputs of the combined SAPs. Furthermore, the system beamformer channel may be configured to provide a delay based on a "virtual" element location, where the virtual element may be typically be chosen as the center of mass for all the active transducer elements which contribute to the signal for that channel. FIG. 13 depicts a location of the virtual element 312 for an example configuration 310 in which two diagonally disposed SAPs indicated by 'B' are connected to the same channel 'B' 252. Further, FIG. 14 illustrates an example configuration 314 having several possible "virtual" element locations for many different QuadSAP configurations. Moreover, as illustrated in FIG. 14, it may be noted that the control of delays in the individual SAPs should account for various configuration possibilities.

Thus far, the examples of SAP configurations illustrated in FIGS. 5-14 have illustrated a "square" shaped geometry for a QuadSAP with individual 4×4 SAPs. In accordance with aspects of the present technique, it may be noted that the idea of flexible output connection may be extended to other configurations of SAPs. Furthermore, the number and arrangement of the exclusive system channels and shared system channels may also be varied.

Figure 16:
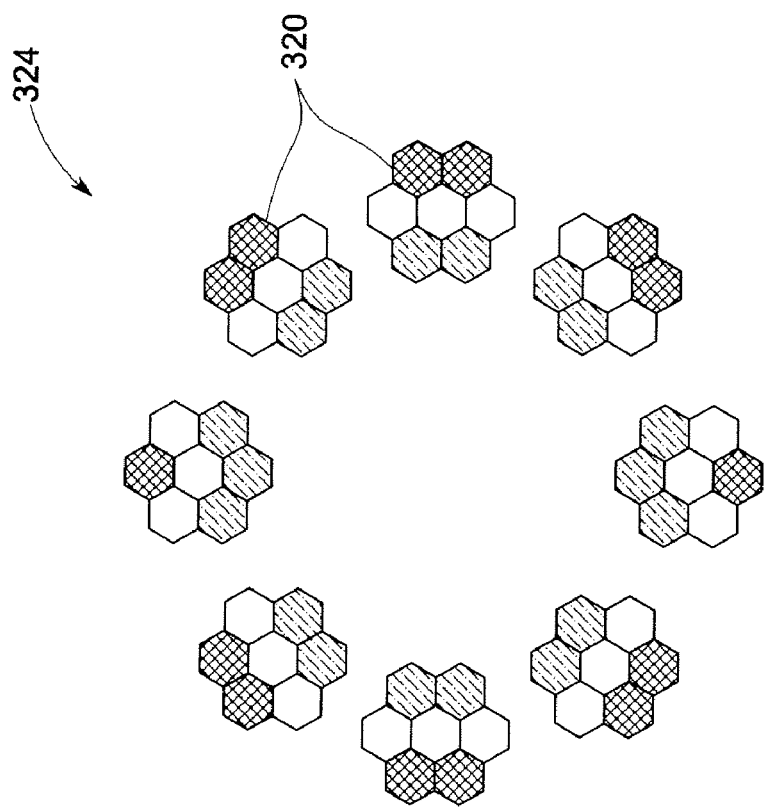
FIG. 16 illustrates various configurations using the hexagonally shaped sub-aperture processors structures of FIG. 15, in accordance with aspects of the present technique.
Figure 15:
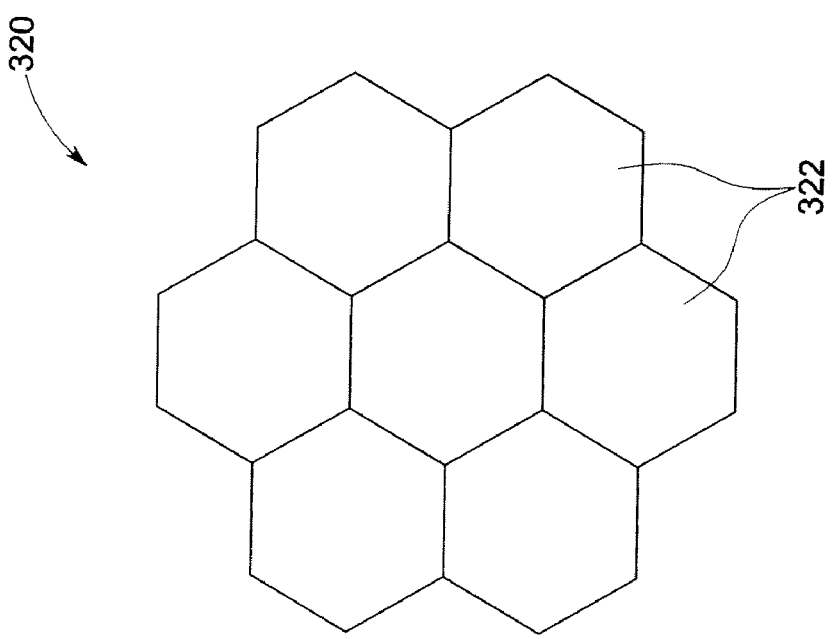
FIG. 15 illustrates another example configuration having hexagonally shaped sub-aperture processors, in accordance with aspects of the present technique.

The size or shape of the sub-apertures (i.e., groups of transducer elements) associated with a given SAP may be different from the 4×4 "square" shaped sub-apertures described with reference to FIGS. 5-14. In other words, the concept of sub-apertures may be configured to be scalable, in accordance with aspects of the present technique. Accordingly, another example configuration 320 is illustrated in FIG. 15, where the SAP package is hexagonally shaped. In this embodiment, the SAP package 320 may include several hexagonally shaped SAPs 322. In addition, sub-apertures that are in operative association with each of the SAPs 322 may be configured to exhibit a hexagonal shape. Further, the sub-apertures may be configured to include a determined number of transducer elements. In a presently contemplated configuration, a group of seven SAPs and their associated hexagonal sub-apertures may be grouped together to form a SuperSAP structure 320 illustrated in FIG. 15. This SuperSAP structure 320 may include three system channels, in certain embodiments. Moreover, FIG. 16 also illustrates some possible configurations using this SuperSAP structure 320 of FIG. 15. It may be noted that in accordance with aspects of the present technique, system channels may also be shared also between SuperSAPs 320 in all directions.

By implementing the SuperSAP structure as described hereinabove, an optimal delay range across the hexagonally shaped SAP sub-apertures may be achieved.

FIG. 17 illustrates another example configuration 330 of a SAP package, where the SAP 330 package is square shaped. In this embodiment, the SAP package 330 may include several square shaped SAPs 332 arranged in a 4×4 pattern. In addition, sub-apertures that are in operative association with each of the SAPs 332 may be configured to exhibit a square shape. Also, the sub-apertures may be configured to include a determined number of transducer elements.

Turning now to FIG. 18, yet another example configuration 334 of a SAP package is illustrated. In this configuration, the SAP package 334 is configured to exhibit a rectangular shape. The SAP package 334 may include several square shaped SAPs 336 arranged in a rectangular pattern. It may be noted that sub-apertures that are in operative association with each of the SAPs 336 may be configured to exhibit a square shape. Additionally, the sub-apertures may be configured to include a determined number of transducer elements.

Referring now to FIG. 19, a further example configuration 338 of a SAP package is illustrated. In the example illustrated in FIG. 18, the SAP package 338 is configured to exhibit a triangular shape. The SAP package 338 may include several square shaped SAPs 340 arranged in a triangular pattern. It may be noted that sub-apertures that are in operative association with each of the SAPs 340 may be configured to exhibit a square shape. Additionally, the sub-apertures may be configured to include a determined number of transducer elements.

The various transducer assemblies, system for imaging and method of imaging using the exemplary transducer assembly described hereinabove allow a probe and system based on combined sub-aperture and system beamforming to have an increased ratio of transducer area per system channel while minimizing beamforming delay errors and preserving image quality. For a fixed number of system channels, the above arrangement allows a larger or more finely divided acoustic aperture, resulting in improved beam steering and resolution. Alternatively, the arrangement described hereinabove allows operating larger or more complex transducer arrays with systems that have relatively few beamforming channels, potentially leading to 2D transducer arrays and real-time 4D imaging on compact and portable ultrasound systems.

Additionally, since the systems and method described hereinabove are based on switching the outputs of the SAPs rather than their inputs, the number of switching elements may be greatly reduced. Consequently the performance of the system may be dramatically enhanced as the system is robust against impedance mismatches, noise, parasitics and other problems that may be caused by introducing switches into the sensitive signal path between the transducer elements and the SAP input preamplifiers. Additionally, use of the transducer assembly described hereinabove may also result in simplified control.

Furthermore, as the outputs of the SAPs are connected to the system channels by switching elements, thereby facilitating coupling the outputs of at least two SAPs to at least one system channel. Also, the SAP configurations may be chosen to optimize image quality. In addition, the configuration of the SAPs may be set globally based upon the beam direction. Moreover, the local beam direction may be employed to set varied configurations across the transducer array.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

What is claimed is:

1. An ultrasound transducer assembly, comprising:
   a transducer array comprising a plurality 'M' of transducer elements;
   a sub-aperture processor comprising a plurality 'P' of input channels and an output channel, wherein the plurality 'P' of input channels is coupled to the 'M' transducer elements; and
   a plurality 'R' of switching elements in operative association with the output channel of the sub-aperture processor to switchably couple the output channel to any combination of a plurality of 'N' system channels.

2. The transducer assembly of claim 1, further comprising control circuitry coupled to the plurality 'R' of switching elements and configured to control selection of the at least one system channel to be operatively coupled with the output channel of the sub-aperture processor.

3. The transducer assembly of claim 2, wherein the output channel of the sub-aperture processor is operatively coupled to the at least one system channel based upon a local sub-aperture geometry, a beam geometry, or a combination thereof.

4. The transducer assembly of claim 1, wherein the plurality 'P' of input channels is different from the plurality 'M' of transducer elements.

5. The transducer assembly of claim 1, wherein the transducer assembly is configured for use in an invasive probe, and wherein the invasive probe comprises an imaging catheter, an endoscope, a laparoscope, a surgical probe, a transesophageal probe, a transvaginal probe, a transrectal probe, an intracavity probe, or a probe adapted for interventional procedures.

6. An ultrasound transducer assembly, comprising:
   a plurality 'K' of sub-aperture processors, wherein each of the 'K' sub-aperture processors comprises a plurality of input channels and an output channel;
   a plurality 'R' of switching elements in operative association with the output channel of each sub-aperture processor;
   wherein the transducer assembly is configured such that each output channel is switchably connectable to a plurality 'N' of system channels.

7. The transducer assembly of claim 6, further comprising a plurality of switching elements in operative association with the output channel of each of the 'K' sub-aperture processors and configured to switchably couple the output channels to at least one of the 'N' system channels.

8. The transducer assembly of claim 7, wherein the K sub-aperture processors are independently configured to be switchably coupled to a system channel based on a local steering direction.

9. The transducer assembly of claim 7, wherein the K sub-aperture processors are independently configured to be switchably coupled to a system channel based on a global steering direction.

10. The transducer assembly of claim 7, wherein the sub-aperture processors are logically grouped into a first Quad-SAP having a corresponding first QuadSAP output channel, and wherein the first QuadSAP output channel is coupled to an exclusive system channel dedicated to the first QuadSAP.

11. The transducer assembly of claim 7, wherein the sub-aperture processors are logically grouped into a first Quad-SAP having a corresponding first QuadSAP output channel, and the first QuadSAP output channel is coupled to an exclusive system channel dedicated to the first QuadSAP, and a shared system channel coupled to other QuadSAPs.

12. The transducer assembly of claim 11, wherein the shared system channel is further coupled to a second QuadSAP, where at least one of the transducer elements coupled to the second QuadSAP is physically neighboring at least one of the transducer elements coupled to the first QuadSAP.

13. The transducer assembly of claim 7, further comprising control circuitry coupled to the plurality of switching elements and configured to control selection of the at least one system channel to be operatively coupled to the at least one output channel of each of the 'K' sub-aperture processors.

14. The transducer assembly of claim 13, wherein the at least one output channel of each of the 'K' sub-aperture processors is operatively coupled to the plurality 'N' of system channels based upon a local sub-aperture geometry, a beam geometry, or a combination thereof.

15. The transducer assembly of claim 14, wherein a sub-group of sub-aperture processors is selected to be operatively coupled to a system channel based upon a determined beam-forming delay.

16. The transducer assembly of claim 6, wherein the 'K' sub-aperture processors are grouped in a single package.

17. An ultrasound system, comprising:
an acquisition subsystem configured to acquire ultrasound data, wherein the acquisition subsystem comprises:
a transducer array comprising a plurality 'M' of transducer elements;
a plurality 'N' of system channels, a sub-aperture processor comprising a plurality 'P' of input channels and an output channel, wherein the plurality 'P' of input channels is coupled to the 'M' transducer elements;
a plurality 'R' of switching elements in operative association with the output channel of the sub-aperture processor to switchably couple the output channel to any combination of the 'N' system channels; and
a processing subsystem configured to process the ultrasound data acquired via the acquisition subsystem.

18. The transducer assembly of claim 17, wherein the 'M' transducer elements are grouped in a determined pattern, wherein the determined pattern comprises a rectangular shape, a triangular shape, a hexagonal shape, or a combination thereof.

19. The transducer assembly of claim 17, further comprising a plurality of sub-aperture processors wherein each of the plurality 'N' of system channels is switchably connectable to one or more sub-aperture processors at a given time.

20. A method of imaging, comprising:
receiving by a first plurality of ultrasound transducer elements, one or more signals representative of imaging data;
processing the one or more signals by a first sub-aperture processor coupled to the first plurality of transducer elements; and
switchably coupling an output signal from the first sub-aperture processor to any combination of a selected plurality of system channels.

21. The method of claim 20, further comprising:
receiving by a second plurality of transducer elements, one or more signals representative of imaging data;
processing the one or more signals by a second sub-aperture processor coupled to the second plurality of transducer elements; and
switchably coupling output signals from the first and second sub-aperture processors to at least one shared system channel.

22. The method of claim 21, wherein the output signals from the first and second sub-aperture processors are switchably coupled based at least in part upon a determined beam geometry, beam direction, a transducer element geometry, or a combination thereof.

23. The method of claim 22, wherein the output signals from the first and second sub-aperture processors are switchably coupled to the system channels based upon an orientation of corresponding transducer elements to the beam.

24. The method of claim 23, wherein the output signals of the first and second sub-aperture processors that are disposed in a direction substantially orthogonal to a direction of the beam are switchably coupled to the same system channel.

25. The method of claim 22, wherein the output signals from the first and second sub-aperture processors are switchably coupled to the system channels so as to optimize image quality.

* * * * *

UNITED STATES PATENT AND TRADEMARK OFFICE
CERTIFICATE OF CORRECTION

PATENT NO. : 7,775,982 B2  Page 1 of 1
APPLICATION NO. : 11/611423
DATED : August 17, 2010
INVENTOR(S) : Hazard et al.

It is certified that error appears in the above-identified patent and that said Letters Patent is hereby corrected as shown below:

In Column 7, Line 64, delete "(134, 136, 138)" and insert -- (132, 134, 136, 138) --, therefor.

Signed and Sealed this

Twenty-eighth Day of September, 2010

David J. Kappos
*Director of the United States Patent and Trademark Office*